(12) United States Patent
Feng

(10) Patent No.: US 6,463,120 B1
(45) Date of Patent: Oct. 8, 2002

(54) X-RAY MEASUREMENT OF RESIN DISTRIBUTION IN A CELLULOSIC MATERIAL

(75) Inventor: Martin W. Feng, Vancouver (CA)

(73) Assignee: Forintek Canada Corp., Vancouver (CA)

(*) Notice: Subject to any disclaimer, the term of this patent is extended or adjusted under 35 U.S.C. 154(b) by 0 days.

(21) Appl. No.: 09/775,114

(22) Filed: Feb. 1, 2001

(51) Int. Cl.$^7$ .............................................. G01N 23/273
(52) U.S. Cl. ......................................... 378/45; 378/44
(58) Field of Search .............................. 378/44, 45, 47; 156/64, 67; 252/408.1, 301.16, 1, 700

(56) References Cited

U.S. PATENT DOCUMENTS 5,359,024 A * 10/1994 Kierkels et al. ............ 528/129
5,830,769 A * 11/1998 Wieder et al. ............... 436/172

FOREIGN PATENT DOCUMENTS

WO    WO-97/25144 A1 *  7/1997

OTHER PUBLICATIONS

Kasper, et al., "Determination of Resin Distribution in Flakeboard Using X-Ray Spectrometry," Forest Products Journal vol. 30, No. 7, pp. 37–40.

Johansson, et al., "A Method for the Analysis of the Glue Efficiency in Particleboards," Trätek, Rapport I 9112076, Stockholm 1991.

Wood Adhesives 2000 Entended Abstracts, "Measurement of resin Distribution in MDF Fiber," Kamke, et al., and "Chemistry, Use, and Advantages of Melamine–Based Wood Adhesives," van der Waals, et al., pp 39 and 40.

Bolton, A.J.,et al., The Microdistribution of UF Resins in Particleboard, Symposium on Forest Products Research International—Achievements and the Future, Pretoria Apr. 22–26, 1985, Proceedings vol. 6 (17–12), pp. 1–19.

* cited by examiner

Primary Examiner—David P. Porta
(74) Attorney, Agent, or Firm—Christie, Parker & Hale, LLP

(57) ABSTRACT

A method for measuring bonding agent content and distribution in a composite product that includes bonding agent and cellulosic material. The method involves using a bonding agent that includes electronegative functional groups and an X-ray active cationic label bonded with the functional groups in the manufacture of the composite product. The cellulosic material is exposed to X-rays to generate a characteristic fluorescence signal from the label. The X-ray fluorescence of the label is measured to determine the amount and distribution of the label in the cellulosic material and thereby the amount and distribution of the bonding agent in the composite product. The present invention also provides a bonding agent composition useful for determining the distribution of the bonding agent in a composite product comprising a bonding agent containing electronegative functional groups and a label compound that includes positively charged ions to emit characteristic fluorescence when exposed to X-rays. The bonding agent and the label compound are homogeneously mixed.

30 Claims, 3 Drawing Sheets

X-RAY MEASUREMENT OF RESIN DISTRIBUTION IN A CELLULOSIC MATERIAL

FIELD OF THE INVENTION

This invention relates to a new system for improved quality and process control in the wood products industry, and in particular, to a system for determining resin distribution in cellulosic material by using a novel labelled resin for detection by x-ray spectrometry.

BACKGROUND OF THE INVENTION

Cellulosic composite products are generally manufactured by organizing cellulosic material, such as particles of wood, straw, bamboo, hemp or the like into a mat of material after coating by a bonding agent, and exposing the resulting mat to pressure and heat to create a finished product such as a board or panel. In the case of wood, the particles can include chips, flakes, fibres or strands. The bonding agent plays a crucial role in determining the strength of the finished product. In the medium density fibreboard and particleboard industry, urea-formaldehyde resins are preferably used. Other resins include melamine-urea-formaldehyde, melamine formaldehyde, and phenol-formaldehyde resins.

The amount of resin added and the overall distribution of the resin are key factors in determining the strength of the finished product. Presently, it is standard practice to blend a pre-determined amount of resin with the cellulosic material and test samples of the resulting product to determine strength properties. Depending on strength test results, the amount of resin added is adjusted downwardly to lower the strength of the product while reducing cost or adjusted upwardly to increase strength and costs. Resin is among the costliest components of a composite cellulosic product and being able to reduce the amount of resin while ensuring that the final product meets quality control and assurance guidelines is a sought after goal in the industry.

Using less resin requires that the resin be distributed as efficiently as possible in the finished product. Reliable measurement of resin distribution has been a long standing problem for the industry particularly with respect to composite wood products which represent the majority of products produced. The problem has been particularly difficult for the medium density fibreboard and particleboard industry which use urea-formaldehyde resins. No reliable and effective non-destructive test method for the detection and measurement of the resin is currently known. Urea-formaldehyde resin is nearly colourless when viewed in white light. Phenol-formaldehyde resin has a distinctive red-brown colour, but when it appears in a thin layer, it is also difficult to detect against a brown coloured wood background. Visual inspection systems are therefore not appropriate for determining resin distribution.

Work has been conducted to discover reliable methods for determining resin distribution. For example, Kasper & Chow (1980) in their paper entitled *Determination of Resin Distribution in Flakeboard Using X-Ray Spectrometry*, Forest Products Journal 30(7):37–40, examined phenol-formaldehyde resin distribution in wood flakes using bromide as a label and X-ray spectrometry as a detection tool. Using bromide as a label for resins has some fundamental limitations for detection and measurement of resin distribution. In particular, bromide is negatively charged and is therefore, not strongly attracted to the resin molecules which have many highly electronegative functional groups. Therefore, bromide will tend not to stay with the resin molecules throughout the board manufacturing process. In addition, bromide is highly water soluble and will tend to migrate through the wood flakes along with water. The factors impose serious limitations on bromide as a resin label.

Johansson et al. (1991) in a paper entitled *A Method for the Analysis of the Glue Efficiency in Particleboards* Trätek, Rapport I 9112076, Stockholm describe how they developed a method for the analysis of resin efficiency in particleboard using copper sulphate and rubeanic acid. The test method is destructive in that it turns the resinated material black to indicate the presence of resin. Such a method has great limitations for developing into a practical test method for both on-line and off-line measurement of resin distribution in the composite wood product industry.

The most current work to develop an effective and reliable method of detecting urea-formaldehyde resin distribution has been undertaken by Kamke. In a paper presented at the Wood Adhesives 2000 meeting, Kamke discussed using fluorescent dyes to track resin distribution, however, the results of initial test were inconclusive.

SUMMARY OF THE INVENTION

Good resin distribution is key to the manufacture of high quality cellulosic products, and, in particular, composite wood products at reasonable cost. There is a need for a reliable method of monitoring resin distribution in order that the distribution can be optimized during the resin blending and application process.

The present invention addresses the problem of measuring resin distribution by providing a non-destructive method of determining resin content and distribution. Accordingly, the present invention provides a method for measuring bonding agent content and distribution in a cellulosic material mixed with the bonding agent comprising the steps of:

using a bonding agent that includes electronegative functional groups and an X-ray active cationic label bonded with the functional groups;

exposing the cellulosic material to X-rays to generate a characteristic fluorescence signal from the label; and measuring the X-ray fluorescence of the label to determine the amount and distribution of the label in the cellulosic material and thereby the amount and distribution of the bonding agent in the cellulosic material.

In a further aspect, the present invention provides a bonding agent composition useful for determining the distribution of the bonding agent in a cellulosic material mixed with the bonding agent comprising:

a bonding agent containing electronegative functional groups; and a label compound that includes positively charged ions to emit characteristic x-ray fluorescence when exposed to X-rays, the bonding agent and the label compound being homogeneously mixed.

Preferably, the bonding agent will be a water based resin that contains electronegative functional groups and the label compound will contain an X-ray active metallic ion. To trace bonding agent distribution successfully, it is essential that the label stays with the bonding agent at all times during and after the manufacturing process. The metallic ions are positively charged and form strong bonds with the highly electronegative functional groups of the resin molecules to move with the resin as the resin is distributed during the manufacturing process. Subsequently, the metallic ions can be located and measured by X-ray fluorescence and converted to resin content by a standard calibration curve.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

The method of the present invention finds general application in measuring bonding agent distribution when the agent is mixed with cellulosic material. Such cellulosic material includes, but is not limited to, particles of wood, straw, bamboo and hemp which are used to make composite products such as panels and boards. The description and examples below relate generally to measuring resin distribution in composite wood products formed from wood particles such as chips, flakes, strands, fibres or the like. It will be apparent to those skilled in the art that the method and bonding agent composition of the present invention can be used in the manufacture of any composite products made by mixing cellulosic material and a bonding agent which includes highly electronegative functional groups.

Figure 1:
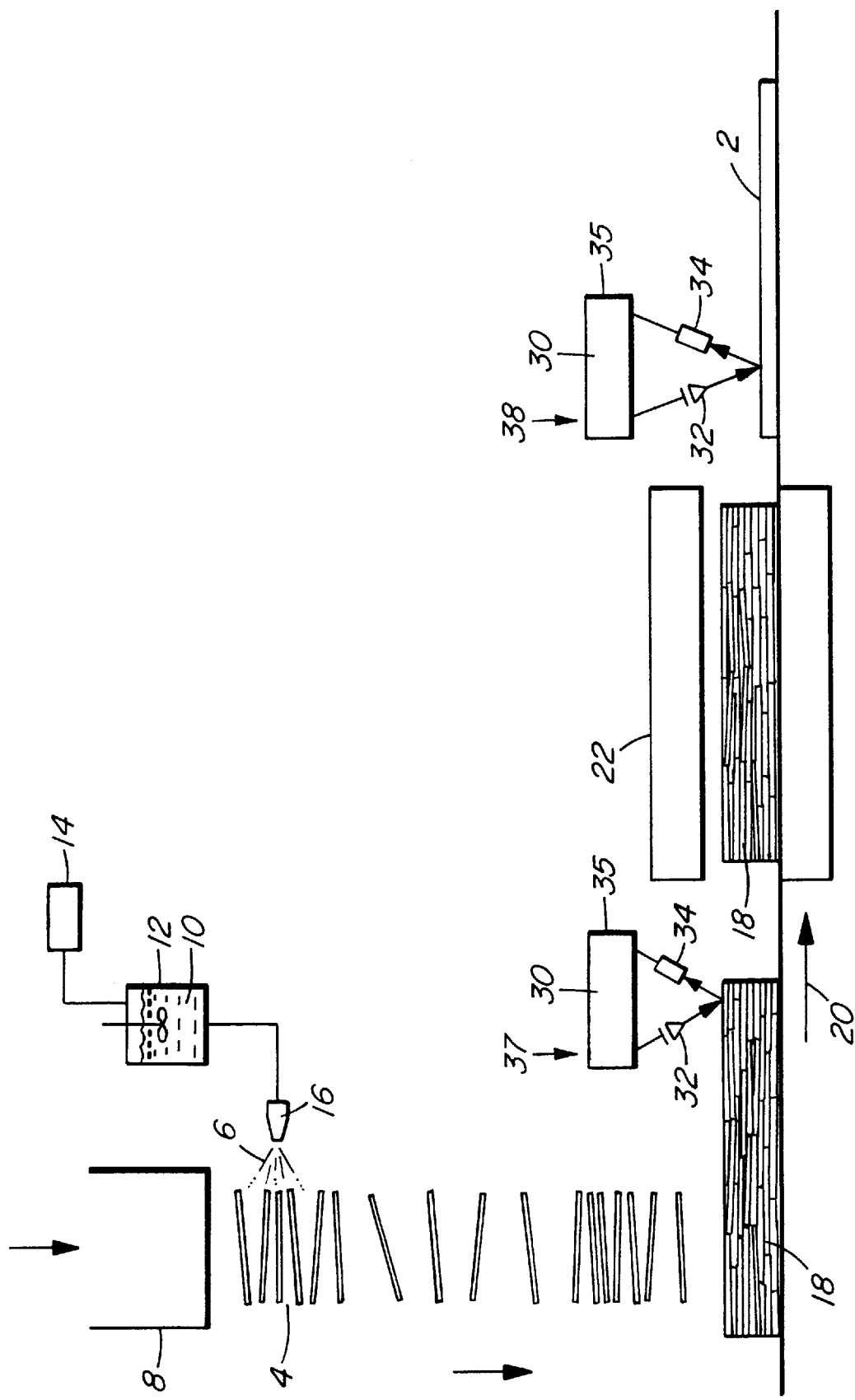
FIG. 1 is a schematic view of a production line for manufacturing a composite wood product according to the method of the present invention.

Referring to FIG. 1, there is shown schematically the general process for manufacturing a finished composite wood product 2 from wood furnish and a bonding agent. Depending on the wood product to be manufactured, the wood furnish will be in the form of chips, flakes, strands, fibres or the like. Strands 4 are illustrated for convenience in FIG. 1. The strands are supplied from a source of wood furnish 8 that is replenished by cutting and processing of raw logs.

The bonding agent is preferably a resin 10 selected for having a chemical composition that includes electronegative functional groups. This includes resins such as urea-formaldehyde, melamine-urea-formaldehyde, melamine-formaldehyde and phenol-formaldehyde which are commonly used in various cellulosic products. Modified versions of these resins are also used. Modified resins are generally commercial resins that have additives such as ammonia, salt, sugar or molasses intended to improve some specific properties of the resin. All these resins and modified versions have strongly electronegative functional groups. Resin 10 is held in a storage tank 12.

An X-ray active label selected to bond with the electronegative functional groups of the resin can be added to the resin. The X-ray active label is preferably a metallic ion that generates a characteristic fluorescence signal when exposed to X-ray. The metallic ion is positively charged and forms strong bonds with the electronegative functional groups of the resin molecules to move with the resin as the resin is distributed during the manufacturing process. The cation is supplied in the form of a water soluble compound that is added to the resin either during or after the resin manufacturing process. Suitable cations include $Cu(II+)$, $Ba(II+)$, $Na(I+)$ and $K(I+)$. The cations are mixed with the bonding agent in sufficient quantity to create an ion concentration in the resin capable of emitting detectable amounts of x-ray fluorescence.

In some cases, the label cations are already present in the resin. For example, $Na(I+)$ cations exist in phenol-formaldehyde resin (resol resin) and do not need to be added to the resin.

In FIG. 1, the cation is shown being added to resin 10 in tank 12 from a cation supply tank 14 such that tank 12 acts as a mixing vessel. The cation is homogeneously mixed with the resin under agitation. The water soluble compound supplying the cation is added to the resin in an amount not to cause sedimentation or precipitation. The result is a novel homogeneous resin composition containing an X-ray active label.

The resin composition is applied as a solution to the cellulosic material in the form of wood furnish in the example of FIG. 1. The resin solution 6 is applied to wood strands 4 by sprayer 16. Alternatively, resin solution 6 can be applied by immersing the strands in a bath. Other conventional methods of applying resin to the wood furnish can also be used.

After applying the resin solution to the wood furnish in the form of strands 4, the strands are conveyed to form an organized mat 18 of stacked strands.

Mat 18 is then advanced in the direction of arrow 20 to hot press 22. In press 22, heat and pressure are applied to the mat to compress and bond the wood furnish together to create finished composite wood product 2. Hot press 22 can be a continuous press or a batch press. A batch press is shown in FIG. 1. In the event that a continuous press is used, mat 18 is formed and conveyed to press 22 on a continuous basis.

At certain stages in the production of the composite product, the cellulosic material is exposed to X-rays to generate X-ray fluorescence signals from the label in the resin. These signals are measured to determine the distribution of the label in the product. Using calibration curves, the amount of label measured by X-ray fluorescence can then be converted to resin content and distribution.

Figure 2:
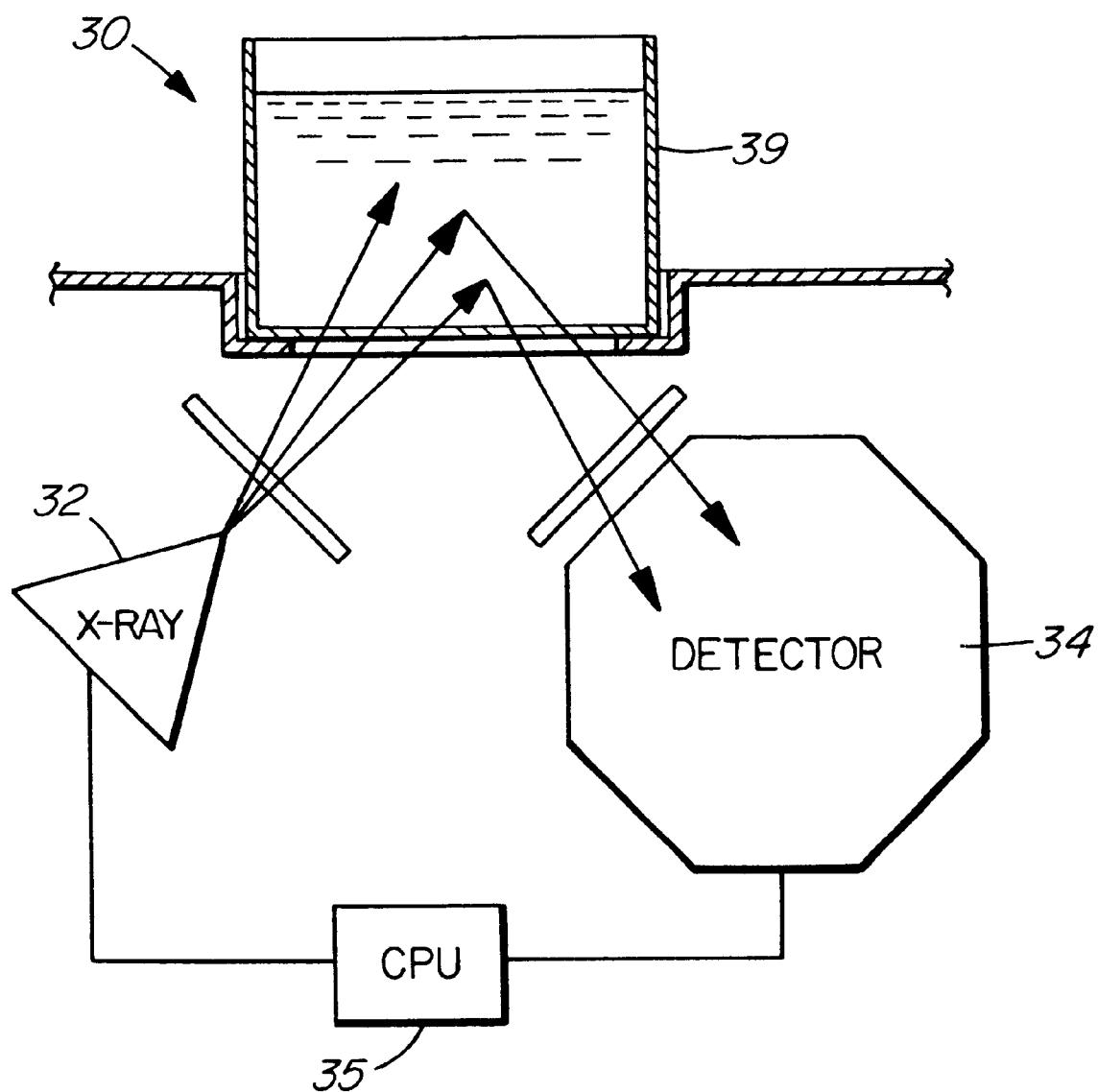
FIG. 2 is a schematic view of the X-ray scanning and detecting apparatus for use in scanning samples according to the present invention.
Figure 3:
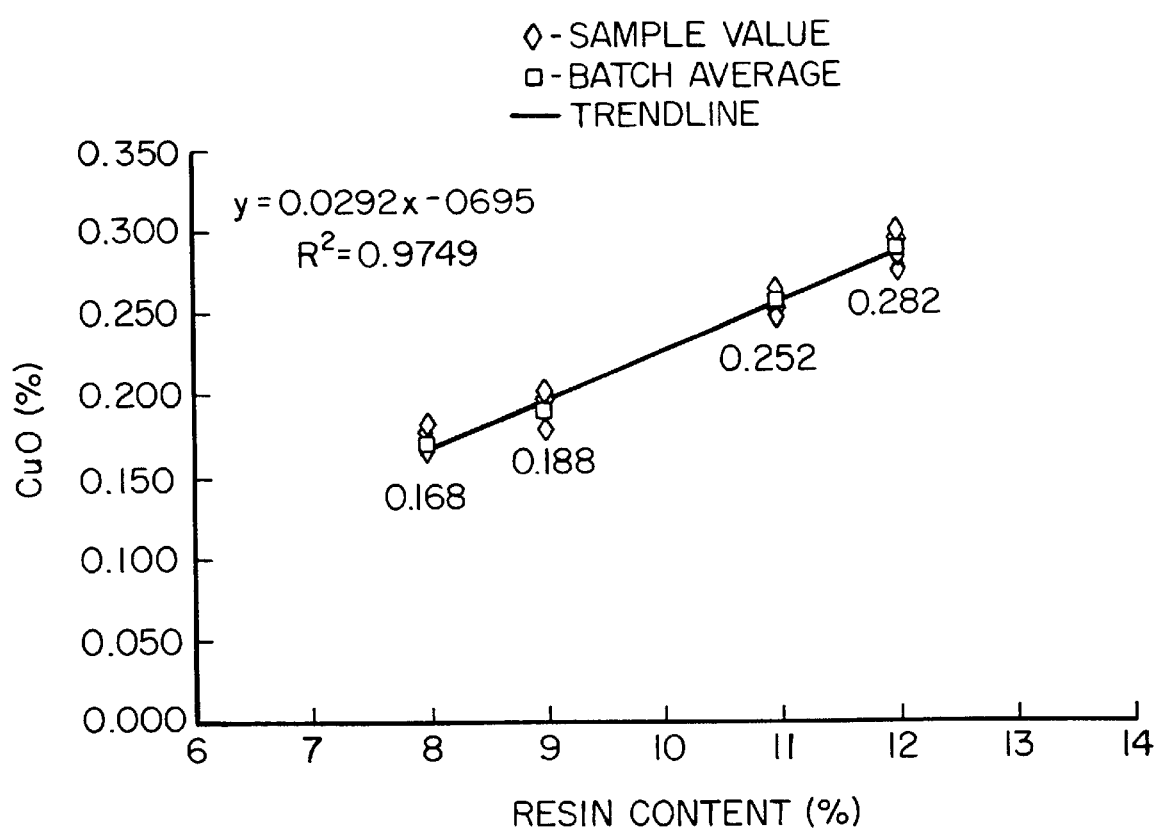
FIG. 3 is a sample calibration curve showing the relationship between measured copper concentration and resin content.

FIG. 1 and 2 show exemplary X-ray generation and detection units 30. Each unit includes an X-ray source 32 to direct X-rays to the cellulosic material to cause the metallic ions to fluoresce and an X-ray detector 34 to detect the fluorescence signals. The generation and detection of X-rays is preferably controlled by a central processing unit 35 running an appropriate control programme. FIG. 3 illustrates an example calibration curve that can be incorporated into the control programme as a look-up table to convert measured metal ion concentrations into resin content. In the example of FIG. 3, Cu (II+) ions as a CuO percent of the total weight of the sample are plotted against resin solids content as a percent total weight of the sample. Based on testing, it has been determined that different calibration curves exist for different solids contents of the same resin. Therefore, it is necessary to monitor the solids content of the resin and input the resin and solids content into the computer programme to ensure accurate results.

Preferably, central processing unit 35 will display resin distribution measurement results in an easy to read manner on a video display unit. The metallic ion concentrations can be easily converted to resin concentrations by a function button that applies the calibration curve and displays the resin concentration results.

The X-ray units 30 of FIG. 1 are positioned to operate on a continuous on-line basis during the manufacture of the composite wood product. The unit positioned at location 37, before the hot press, operates to measure the resin content and distribution of mat 18 on an on-line basis as the manufacturing process is on going. Similarly, the unit positioned at location 38, after the hot press, operates to measure the resin content and distribution of the finished composite wood product as the product is manufactured.

Resin distribution measurements can also be conducted using the X-ray units on an off-line basis. Generally, this involves selecting samples from the manufacturing line for testing. The X-ray unit illustrated in FIG. 2 is specifically designed to handle test samples. A sample holder 39 is provided to securely hold the sample of material to be analyzed in place while X-ray scanning occurs using X-ray source 32 and detector 34.

Off-line scanning of random samples of resinated cellulosic material can be performed immediately after resin is applied to the wood particles to check for resin content and the evenness of distribution at an early stage in the manufacturing process. After hot pressing, the finished composite wood product can be randomly sampled and evaluated in an off-line X-ray unit to determine resin content and distribution.

Some specific examples of the method of the present invention using specific resin compositions will serve to further clarify the present invention:

EXAMPLE 1

The method of the present invention can be used to study and monitor the manufacture of medium density fibreboard (MDF) with urea-formaldehyde resin, melamine-urea-formaldehyde resin or phenol-formaldehyde resin. Monitoring of the resin content and distribution can be conducted for both the resinated wood furnish and the MDF panels on an on-line or off-line basis.

For example, in the manufacture of MDF using urea-formaldehyde resin, a water solution of cupric sulphate is added to the resin dilution tank with agitation so that the Cu(II+) concentration in the resin is about 0.2% of the resin solids content. The pH of the resulting homogeneous resin solution is lowered due the addition of cupric sulphate. Alternatively, the source of cations can be a solution of cupric chloride or cupric nitrate. The resulting homogeneous resin solution is then blended with the wood fibres in a conventional manner. The resinated fibres are then sampled randomly, and the samples used to monitor resin content and distribution based on scanning of the samples by an off-line X-ray unit programmed with an appropriate calibration curve. Alternatively, an on-line X-ray unit can be installed before the hot press to measure the mat resin content continuously. After hot pressing, the boards are sampled randomly, and the samples used to monitor the resin content and distribution in the finished MDF product based on scanning of the board samples by an off-line X-ray unit. Alternatively, an on-line X-ray unit can be used after the hot press to monitor the board resin content and distribution on a continuous basis as the board is produced.

EXAMPLE 2

The method of the present invention can be used to study and monitor the manufacture of particleboard with urea-formaldehyde resin, melamine-urea-formaldehyde resin or phenol-formaldehyde resin. Monitoring of the resin content and distribution can be conducted for both the resinated wood furnish and the particleboard panels on both an on-line or off-line basis.

For example, in the manufacture of particleboard using urea-formaldehyde resin, a water solution of cupric sulphate is added to the urea-formaldehyde resin dilution tank with agitation so that the Cu(II+) concentration in the resin is about 0.4% of the resin solids content. The pH of the resulting homogenous resin solution is lowered due to the addition of cupric sulphate. The resulting homogeneous resin solution is then applied to the wood furnish in a conventional manner. The resinated furnish is then sampled randomly, and the samples used to monitor resin content and distribution based on scanning of the samples by an off-line X-ray unit programmed with an appropriate calibration curve. Alternatively, an on-line X-ray unit can be installed before the hot press to measure the mat resin content continuously. After hot pressing, the boards are sampled randomly, and the samples used to monitor the resin content and distribution in the finished particleboard product based on scanning of the board samples by an off-line X-ray unit. Alternatively, an on-line X-ray unit can be used after the hot press to monitor the board resin content and distribution on a continuous basis as the board is produced.

EXAMPLE 3

The method of the present invention can be used to study and monitor the manufacture of oriented strand board (OSB) with phenol-formaldehyde resin (resol type in either liquid or powder form). Monitoring of the resin content and distribution can be conducted for both the resinated wood strands and the OSB panels on both an on-line or off-line basis.

In this case, the label is the Na(I+) ion existing in the resol resin. The resin solution is applied to the wood strands in a conventional manner. The resinated strands are then sampled randomly, and the samples used to monitor resin content and distribution based on scanning of the samples by an off-line X-ray unit programmed with an appropriate calibration curve. Alternatively, an on-line X-ray unit can be installed before the hot press to measure the mat resin content and distribution continuously. After hot pressing, the boards are sampled randomly, and the samples used to monitor the resin content and distribution in the finished OSB product based on scanning of the board samples by an off-line X-ray unit. Alternatively, an on-line X-ray unit can be used after the hot press to monitor the board resin content and distribution on a continuous basis as the board is produced.

Although the present invention has been described in some detail by way of example for purposes of clarity and understanding, it will be apparent that certain changes and modifications may be practised within the scope of the appended claims.

I claim:

1. A method for measuring bonding agent content and distribution in a cellulosic material mixed with the bonding agent comprising the steps of:

using a bonding agent that includes electronegative functional groups and an X-ray active cationic label bonded with the functional groups;

exposing the cellulosic material to X-rays to generate a characteristic fluorescence signal from the label; and measuring the X-ray fluorescence of the label to determine the amount and distribution of the label in the cellulosic material and thereby the amount and distribution of the bonding agent in the cellulosic material.

2. A method as claimed in claim 1 including the step of converting the amount of the label in the cellulosic material to the amount of bonding agent using a calibration curve.

3. A method as claimed in claim 1 in which the bonding agent is a resin having electronegative functional groups and the label is metallic cations.

4. A method as claimed in claim 3 in which the label is Cu(II+) ions.

5. A method as claimed in claim 4 in which the Cu(II+) ions are provided by a source selected from the group consisting of an aqueous solution of cupric sulphate, cupric chloride and cupric nitrate.

6. A method as claimed in claim 3 in which the label is Ba(II+) ions.

7. A method as claimed in claim 3 in which the label is Na(I+) ions.

8. A method as claimed in claim 3 in which the label is K(I+) ions.

9. A method as claimed in claim 3 in which the cellulosic material is selected from the group consisting of wood, straw, bamboo and hemp.

10. A method as claimed in claim 1 in which the cellulosic material is formed into a composite product.

11. A method as claimed in claim 1 in which the cellulosic material is at an intermediate stage in the manufacture of a composite product.

12. A method as claimed in claim 3 in which the bonding agent is a resin selected from the group consisting of urea-formaldehyde, melamine-urea-formaldehyde, melamine-formaldehyde and phenol-formaldehyde resins.

13. A method as claimed in claim 1 in which the steps of exposing the cellulosic material to X-rays and measuring the X-ray fluorescence of the label are conducted on a continuous on-line basis during the manufacture of a composite product.

14. A method as claimed in claim 1 in which the steps of exposing the cellulosic material to X-rays and measuring the X-ray fluorescence of the label are conducted on an off-line basis to selected samples of the cellulosic material during the manufacture of a composite product.

15. A method as claimed in claim 1 including the additional step of adding the X-ray active cationic label to the bonding agent.

16. A method as claimed in claim 1 in which the X-ray active cationic label is a natural constituent of the bonding agent.

17. A bonding agent composition comprising:
a bonding agent for cellulosic material containing electronegative functional groups; and
a label compound that includes positively charged ions to emit characteristic x-ray fluorescence when exposed to X-rays, the bonding agent and the label compound being homogeneously mixed such that measurement of the X-ray fluorescence of the label compound serves to deter mine the distribution of the bonding agent in the cellulosic material.

18. A bonding agent composition as claimed in claim 17 in which the bonding agent is selected from the group consisting of urea-formaldehyde resin and modified urea-formaldehyde resin.

19. A bonding agent composition as claimed in claim 17 in which the bonding agent is selected from the group consisting of melamine-urea-formaldehyde resin and modified melamine-urea-formaldehyde resin.

20. A bonding agent composition as claimed in claim 17 in which the bonding agent is selected from the group consisting of melamine-formaldehyde resin and modified melamine-formaldehyde resin.

21. A bonding agent composition as claimed in claim 17 in which the bonding agent is selected from the group consisting of phenol-formaldehyde resin or modified phenol-formaldehyde resin.

22. A bonding agent composition as claimed in claim 17 in which the label compound is mixed with the bonding agent in sufficient quantity to create an ion concentration capable of emitting detectable amounts of x-ray fluorescence.

23. A bonding agent composition as claimed in claim 17 in which the label compound is a source of Cu(II+) ions.

24. A bonding agent composition as claimed in claim 23 in which the source of Cu(II+) ions is selected from the group consisting of an aqueous solution of cupric sulphate, cupric chloride and cupric nitrate.

25. A bonding agent composition as claimed in claim 23 in which the label compound is mixed with the bonding agent in sufficient quantity to create a Cu(II+) ion concentration in the bonding agent greater than about 0.1% based on the bonding agent solids content.

26. A bonding agent composition as claimed in claim 17 in which the label compound is a source of Ba(II+) ions.

27. A bonding agent composition as claimed in claim 17 in which the label compound is a source of Na(I+) ions.

28. A bonding agent composition as claimed in claim 27 in which the source of Na(I+) ions is the bonding agent itself.

29. A bonding agent composition as claimed in claim 17 in which the label compound is a source of K(I+) ions.

30. A bonding agent composition as claimed in claim 29 in which the source of K(I+) ions is the bonding agent itself.

* * * * *